United States Patent [19]

McFaul, Sr.

[11] Patent Number: 4,932,397
[45] Date of Patent: Jun. 12, 1990

[54] HEMORRHOIDAL TREATMENT DEVICE

[76] Inventor: Stephen E. McFaul, Sr., 3136 Birch Rd., Philadelphia, Pa. 19154

[21] Appl. No.: 271,596

[22] Filed: NOV. 7, 1988

[51] Int. Cl.⁵ .............................................. A61F 5/24
[52] U.S. Cl. .................................. 128/98.1; 128/887
[58] Field of Search ...................... 128/98.1, 846, 869, 128/883, 884, 885, 887, 889, 891, 168, 171

[56] References Cited

U.S. PATENT DOCUMENTS

| 59,999 | 11/1866 | Harding | 128/834 |
|---|---|---|---|
| 235,959 | 12/1880 | Otto | 128/834 |
| 453,880 | 6/1891 | Coffee | 128/887 |
| 2,574,767 | 11/1951 | Stubbs | 128/834 |
| 2,615,445 | 10/1952 | Holmes | 128/98.1 |
| 2,653,599 | 9/1953 | Bell | 128/98.1 |
| 2,712,821 | 7/1955 | Wolf et al. | 128/98.1 |
| 2,713,340 | 7/1955 | Meminger | 128/98.1 X |
| 2,891,539 | 6/1959 | Hofer et al. | 128/887 X |
| 3,554,184 | 1/1971 | Habib | 128/835 X |
| 3,712,300 | 1/1973 | Davidowitz | 128/98.1 |

Primary Examiner—Mickey Yu
Assistant Examiner—Kevin G. Rooney
Attorney, Agent, or Firm—Richard C. Litman

[57] ABSTRACT

A therapeutic rectal device for alleviating the discomfort of hemorrhoids by protecting the irritated anorectal surfaces from pressure and friction. The rectal device is horseshoe shaped and includes a resilient covering surrounding a core element of malleable material. The device is readily adjustable to conform to the shape and movements of the user's body without displacement, and may be used in combination with hemorrhoidal preparations to promote healing.

5 Claims, 1 Drawing Sheet

HEMORRHOIDAL TREATMENT DEVICE

BACKGROUND OF THE INVENTION

1. Field of the Invention

This invention relates to a device for alleviating the discomfort of hemorrhoids. More particularly, this invention relates to a therapeutic device for effectively assisting in healing hemorrhoids by protecting the irritated anorectal surfaces from pressure and friction.

2. Description of Related Art

Hemorrhoids, or piles as they are commonly known, are an anal-rectal condition which have been the subject of numerous types of treatment for remedying the discomfort associated with them. Medically, hemorrhoids are anorectal swellings composed of varicosities involving one or more of the hemorrhoidal plexus of veins. Pathologically, this anatomical abnormality is a degeneration of the hemorrhoidal plexus, including dilation of the veins and thinning of their walls, resulting in complications such as inflammation, edema, ulceration and thrombosis. Hemorrhoids are characterized by bleeding and protrusions which occur in the lowest portion of the rectum, in the anal canal or at the anal margin.

The general therapy presently available in the art for the treatment of hemorrhoids includes a wide variety of rectally or locally applied medicaments, usually in the form of an ointment or cream or in the form of suppositories. However, the physiological effects of these therapeutically active preparations have not met with great success. Generally, the preparations when administered parenterally are rapidly absorbed and are not properly maintained at the tissues of the affected area for a sufficient duration of time. Furthermore, these drugs when administered rectally are often inactivated or degraded upon application by being entrapped by and assimilated with fecal matter and cannot come in contact with anal surfaces where an hemorrhoidal condition may exist.

It has heretofore been proposed to provide devices which will spread the cheeks of the buttocks apart around the rectal surfaces to prevent contact with the hemorrhoids. One such device is described in U.S. Pat. No. 2,891,539, issued June 23, 1959 to Hofer et al. This patent discloses a generally elongated resilient device having a central opening and medially positioned rib to prevent closure of the opening. The patented device is inserted horizontally and can be securely held in position by a tape attached at the end of the device and applied to the cheeks. However, it is readily apparent from the patent disclosure that the described device would cause appreciable inconvenience to the user and markedly interfere with one's movability. Moreover, the relatively cylindrical device of Hofer, positioned in close proximity to the affected area, is not adjustable to comfortably fit the user and is not provided with any suitable means to prevent displacement, which may cause extreme discomfort and chafing to the irritated area.

Other rectal devices utilized in the treatment of hemorrhoids presently available in the art include medicinal belts and trusses which are adapted to be worn about the abdomen and intended to secure a spread position of the user's buttocks, such as described in U.S. Pat. Nos. 2,615,445 and 2,672,862. Such devices, however, are not entirely satisfactory to the extent that they cannot be worn with complete comfort and those parts of the belt which may come in contact with the anus must be removed and washed and, therefore, cannot be readily maintained in a clean and sanitary condition.

Many sufferers of hemorrhoids, due to the fear and embarrassment with having them treated, frequently improvise self-treatment remedies. Accordingly, hemorrhoid sufferers have attempted to press into the buttocks cleavage, hydrophilic fibers in the form of wadded cellulosic paper or similar materials, but such improvisations afford no significant relief and are apt to become dislodged under minimal activity, such as when the user is walking about or merely sitting.

SUMMARY OF THE INVENTION

It is accordingly a primary object of the present invention to provide an improved device which spreads the cheeks of the buttocks laterally apart to alleviate the discomfort of hemorrhoids and assist in the healing thereof.

It is another primary object of the present invention to provide an improved hemorrhoid treatment device which is readily adjustable to conform to the shape and movements of the user and is reliably maintained in the proper position with complete comfort for extended periods of time without restricting normal activities.

It is among the further objects of the present invention to provide a therapeutic device which is adapted to be coated with a lubricant or hemorrhoidal preparation to prevent chafing and to promote healing; which is simple in construction, economical to manufacture and can be readily replaced after use with a substitute like device; and which does not require tapes or other fastener means to remain reliably positioned within the buttocks cleavage.

These and other objects are accomplished in accordance with the present invention by providing a therapeutic device for alleviating the discomfort of hemorrhoids comprising a generally horseshoe-shaped member having a core element of malleable material and an external covering surrounding the core element. The horseshoe-shaped member includes a pair of laterally spaced-apart side arms depending from a medial bight portion. The core element extends substantially the length of the member, whereby the lateral spacing between the side arms of the horseshoe-shaped member may be manually adjusted to alter the dimensions of the device in accordance with the physical conformation of the user. The external covering provide a cushioning effect, whereby the device when properly positioned within the buttocks cleavage of the user, spreads the cheeks of the buttocks laterally apart to protect irritated anorectal surfaces from pressure and friction.

An advantageous feature of the present invention is a therapeutic device which is reliably retained in place with complete comfort by the resiliency of the side arms of the horseshoe-shaped member in engagement with the interior walls of the buttocks.

The foregoing and other features, advantages and objects of the invention may be more fully appreciated by reference to the following description.

DESCRIPTION OF THE ILLUSTRATIVE EMBODIMENTS

Figure 1:
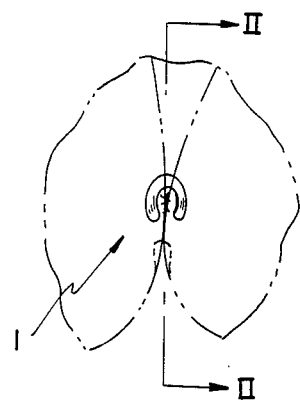
FIG. 1 is a plan view of the therapeutic device according to the present invention in position.
Figure 2:
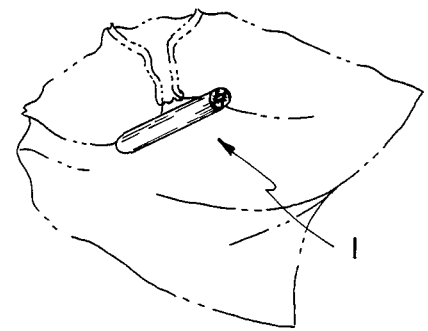
FIG. 2 is a sectional view taken along line II—II of FIG. 1.
Figure 3:
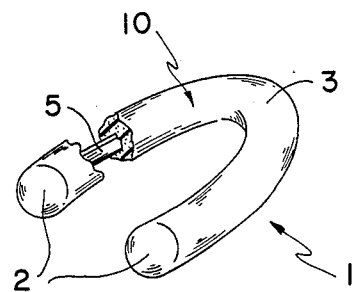
FIG. 3 is a fragmentary perspective view of the therapeutic device according to the present invention.

The therapeutic device of the present invention comprises a horseshoe-shaped member indicated generally as 1 in FIGS. 1, 2 and 3, having a core element 5 (FIG. 3) encased in an external resilient covering 10 (FIG. 3).

The horseshoe-shaped member 1 includes a pair of laterally spaced-apart side arms 2 depending from a medial bight portion 3.

As best shown in FIG. 3, the core element 5 is a flattened elongated strip of malleable material which prevents collapse of side arms 2. An essential characteristic of core element 5 is its capacity to be manually altered, yet retain its altered conformation when subjected to varying pressure and friction, such as applied from the normal activity of the user when the therapeutic device is positioned for use as shown in FIGS. 1 and 2. Any deformable metal exhibiting this essential property would be suitable for purposes of the present invention. Preferably, core element 5 consists of a unitarry strip of soft aluminum measuring approximately 2¼ inches in length, about ⅛ inch in width and about 1/16 inch in thickness before fabrication.

Covering 10 surrounding core element 5, as shown in FIG. 3, preferably comprises a soft, flexible, synthetic form composition which provides a cushioning effect. The covering is generally oval- or circular-shaped in cross section and may consist of a synthetic cellular composition prepared from the polymerization of a polyisocyanate, polyol and forming agent, for example. The device of the present invention may be simply manufactured by conducting the polymerization in the presence of core element 5 by injection-molding and contouring the resulting product into a horseshoe shape.

The described rectal device is designed to prevent the cheeks of the buttocks from rubbing against the inflamed hemorrhoids and has the distinct advantage of being adjustable to conform to the shape and movements of the user's body so that irritation and discomfort are reduced to a minimum. Moreover, the therapeutic device of the present invention may be coated with a lubricant or hemorrhoidal preparations including ointments and creams and may be used in conjunction with suppositories to promote healing.

The foregoing disclosure and description of the invention are illustrative and explanatory thereof, and various changes in the size and materials as well as in the details of the illustrated construction may be made within the scope of the appended claims without departing from the spirit of the invention.

I claim:

1. A therapeutic device for alleviating the discomfort of hemorrhoids comprising;
   a horseshoe-shaped member including a pair of laterally spaced-apart side arms depending from a medial bight portion, said pair of spaced-apart side arms being manually adjustable to alter the dimensions of the device in a co-planar manner and in accordance with the physical conformation of the user,
   said member having a core element of malleable material, said core element having a flattened cross-section allowing for ease of adjustment of said laterally spaced-apart side arms, said cross-section being thinner in a direction defined by a plane containing said spaced apart side arm's,
   an external resilient covering surrounding said core element,
   said covering providing a cushioning effect whereby,
   said member when positioned substantially normal to the anorectal canal within the buttocks cleavage of a user, retains the buttocks laterally spaced apart to protect irritated anorectal surfaces, with said member being reliably maintained in place with said side arms maintained substantially co-planar by the resiliency of said side arms respectively in engagement with the interior walls of the buttocks.

2. The therapeutic device according to claim 1, wherein said core element comprises a deformable metal.

3. The therapeutic device according to claim 1, wherein said external resilient covering includes a soft, flexible, synthetic foam composition.

4. The therapeutic device according to claim 1, wherein said external resilient covering is substantially circular-shaped in cross section.

5. The therapeutic device according to claim 1, wherein said core element comprises a unitary strip of deformable material extending substantially the length of said member.

* * * * *